United States Patent
Juloski et al.

(10) Patent No.: US 8,641,603 B2
(45) Date of Patent: Feb. 4, 2014

(54) COIL SYSTEM FOR THE CONTACT-FREE MAGNETIC NAVIGATION OF A MAGNETIC BODY IN A WORKING SPACE

(75) Inventors: Aleksandar Juloski, Nuremberg (DE); Johannes Reinschke, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 538 days.

(21) Appl. No.: 12/724,597

(22) Filed: Mar. 16, 2010

(65) Prior Publication Data

US 2010/0234685 A1 Sep. 16, 2010

(30) Foreign Application Priority Data

Mar. 16, 2009 (DE) .......................... 10 2009 013 354

(51) Int. Cl.
*A61B 1/00* (2006.01)
*A61B 1/04* (2006.01)
*A61B 1/06* (2006.01)

(52) U.S. Cl.
USPC ............................ 600/117; 600/109; 600/160

(58) Field of Classification Search
USPC .................. 600/117, 118, 109, 160, 424, 300
See application file for complete search history.

(56) References Cited

U.S. PATENT DOCUMENTS

| | | | |
|---|---|---|---|
| 7,019,610 B2 | 3/2006 | Creighton, IV et al. | |
| 7,663,458 B2 | 2/2010 | Reinschke et al. | |
| 8,465,418 B2 * | 6/2013 | Hasegawa et al. | 600/117 |
| 2003/0208107 A1 * | 11/2003 | Refael | 600/300 |
| 2004/0138552 A1 * | 7/2004 | Harel et al. | 600/407 |
| 2004/0236180 A1 * | 11/2004 | Uchiyama et al. | 600/109 |
| 2005/0143642 A1 * | 6/2005 | Minai et al. | 600/407 |
| 2006/0152309 A1 * | 7/2006 | Mintchev et al. | 335/58 |
| 2006/0169293 A1 * | 8/2006 | Yokoi et al. | 128/899 |
| 2007/0106111 A1 * | 5/2007 | Horn et al. | 600/102 |
| 2007/0221233 A1 | 9/2007 | Kawano et al. | |

(Continued)

OTHER PUBLICATIONS

"The Force Model of Wireless Active Actuation for Capsule Endoscope in the GI Tract," Chen et al., Proc. 2007 IEEE Int. Conf. on Robotics and Biominetics, pp. 93-98.

(Continued)

*Primary Examiner* — Philip R Smith
*Assistant Examiner* — William Chou
(74) *Attorney, Agent, or Firm* — Schiff Hardin LLP (57) ABSTRACT

A coil system for the contact-free magnetic navigation of a magnetic body with a magnetic dipole moment in a working chamber, a number of coils and a current control unit for controlling the respective currents in the multiple coils. The current control unit generates a force on the magnetic body in a predefined direction by setting the currents in the multiple coils so that the direction of the force generated by the currents on the magnetic body at each position among a number of positions in a volume in the working chamber essentially corresponds to the predefined direction of force. This coil system has the advantage that the position of the magnetic body in the working chamber does not need to be known exactly in order to move the body in a desired direction or to align the body in a desired orientation direction. This coil system suitable for use in a medical device and by special preference in a device for capsule endoscopy. In this situation, the magnetic body is a capsule that can be navigated in the body of a patient and has an imaging system for capturing images of the internal organs of the patient and a transmit module for sending the captured images to a receiver.

17 Claims, 2 Drawing Sheets

(56) References Cited

U.S. PATENT DOCUMENTS

| | | | |
|---|---|---|---|
| 2007/0244388 A1* | 10/2007 | Sato et al. | 600/424 |
| 2007/0270628 A1 | 11/2007 | Kawano et al. | |
| 2008/0161643 A1* | 7/2008 | Uchiyama et al. | 600/109 |
| 2008/0294006 A1* | 11/2008 | Uchiyama et al. | 600/118 |
| 2008/0300458 A1* | 12/2008 | Kim et al. | 600/118 |
| 2009/0043164 A1* | 2/2009 | Hasegawa et al. | 600/118 |

OTHER PUBLICATIONS

"A Magnetic Stereo Actuation Mechanism for Active Capsule Endoscope," Wang et al., Proc. 29$^{th}$ Annual Int. Conf. of IEEE EMBS (2007), pp. 2811-2814.

* cited by examiner

FIG 1

FIG 2

COIL SYSTEM FOR THE CONTACT-FREE MAGNETIC NAVIGATION OF A MAGNETIC BODY IN A WORKING SPACE

BACKGROUND OF THE INVENTION

1. Field of the Invention

The present invention relates to a coil system and a method for the contact-free magnetic navigation of a magnetic body in a working space.

2. Description of the Prior Art

Coil systems for the contact-free magnetic navigation of a magnetic body employ a plurality of coils to generate a magnetic field which interacts with the magnetic body, as a result of which magnetic forces and torque are generated that bring about the movement of the magnetic body. In this situation, the magnetic force and the magnetic torque which act on the magnetic body can be suitably set by the corresponding currents in the individual coils of the coil system.

In particular, coil systems of the above type are used in the medical field. In this context, a patient is examined by the magnetic body in the working chamber (volume) of the coil system. In this context, the working space is accessible from the outside, and in this space the magnetic forces of the coil system have a sufficient effect on the magnetic body. In order to carry out the examination the magnetic body that is located in the patient and the part of the patient's body that is to be examined are introduced into the working chamber of the coil system. In this situation, the magnetic body constitutes a probe with which measurements can be performed on—in particular images captured of—internal organs of the patient.

A coil system with a magnetic probe is employed for example in gastroenterology, in particular in gastroscopy; see WO 2007/077922 A1. During the endoscopic examination the stomach of the patient is partially filled with water and the patient swallows an appropriate probe that contains a permanent magnet and a camera. The stomach of the patient is located in the working chamber of the coil system, or is introduced into the working chamber after the probe has been swallowed. By using the magnetic forces and torque generated by the coil system, the probe is moved such that captured images of the areas of the patient's stomach lining to be examined are produced. In this situation, it is necessary that a non-homogeneous magnetic field be generated by suitable energization of the coils such that through the interaction of this magnetic field with the permanent magnet in the probe the probe, is suitably positioned and is held in this position.

Different approaches are known for suitably positioning a magnetic body relative to a coil system. A coil system is known from WO 2006/014011 A1, wherein the patient to be examined is moved mechanically with respect to the coil system during the examination. The coil system is constructed such that a single spatial point exists that is fixed with respect to the coil system. If no external forces act on the magnetic body, the body moves toward this spatial point on account of the magnetic forces and torque exerted. When the magnetic body has reached this spatial point, it remains at this spatial point, provided that no forces are exerted from the outside. A disadvantage of this technique is that either the coil system or the patient or both need to be moved mechanically in order to move the magnetic body. This is problematic particularly in the case of applications in which a fast movement of the magnetic body toward a predefined position is required.

Systems are also known in which the coil system is replaced by one or more permanent magnets for moving a magnetic body, see for example U.S. Pat. No. 7,019,610 B2. In these systems also, movement toward a predefined position is achieved by a mechanical movement of the patient, or of the permanent magnet, or of both the patient and the permanent magnet.

Coil systems are furthermore known in which a movement of the magnetic body caused only by the currents in the coil system, without mechanical movement, is achieved by appropriate setting of the magnetic fields and field gradients at the position of the magnetic body (see for example WO 2006/092421 A1). In this situation, however, it is necessary for the position and orientation of the magnetic body to be known, which in turn requires that the position of the magnetic body must additionally be detected.

SUMMARY OF THE INVENTION

An object of the present invention is to circumvent the disadvantages described above of the prior art and to provide a coil system and a method with which it is possible to navigate a magnetic body in contact-free fashion in a simple manner.

The coil system according to the invention has a number of coils and also a current control unit for controlling the respective currents in the multiple coils in order to navigate a magnetic body with a magnetic dipole moment. The current control unit is configured to generate a force on the magnetic body in a predefined direction by the currents in the multiple coils being set during operation of the coil system so that the direction of the force generated by the currents on the magnetic body at each of any position among a number of positions in a volume in the working chamber essentially corresponds to the predefined direction of force. In this manner, a homogeneous alignment of the force in a predefined direction is achieved in a predetermined volume in the working chamber, so that a fixed direction of movement of the body is always ensured in the predetermined volume. The term "predefined direction of force" as used herein means that the direction of force can be set variously by the current control unit. According to the invention, it is possible to dispense with an exact determination of position for the body. The coil system according to the invention additionally has the disadvantage that incorrect movements of the body occur if the measured position has major errors and therefore the current control unit based thereon does not calculate the currents correctly, with the result that the magnetic body moves in an incorrect, undesired direction.

In a preferred embodiment of the coil system according to the invention the current control unit is configured to align the magnetic body in a predefined orientation direction by the currents in the multiple coils being set during operation of the coil system so that the directions of the magnetic field generated by the currents at each position among a number of positions in the volume in the working chamber essentially match and bring about an alignment of the body in the predefined orientation direction. In this situation, the term "predefined orientation direction" means that the orientation direction for the alignment of the magnetic body can be set variously through the current control unit. In the case of a magnetic body which can be rotated with all three degrees of rotatory freedom in the working chamber, the direction of the magnetic field generated by the currents at each position of the number of positions in the volume in the working chamber preferably corresponds essentially to the predefined orientation direction. In this situation, the predefined orientation direction is defined by the direction of the magnetic dipole moment of the magnetic body, which is the direction in which, in the absence of mechanical counteracting forces, the magnetic body always aligns itself so that its magnetic dipole moment runs in the direction of the magnetic field lines of the magnetic field.

Similar to the setting described above of a predefined direction of force, through the establishment of a homogeneous magnetic field direction in a corresponding volume of the working chamber a desired alignment of the body is achieved without the exact position of the body being known. It is thus possible to dispense with a measurement (detection) of the position of the body. Furthermore, no misalignment of the body occurs even in the case of an incorrectly determined position of the body in the working chamber.

In a further preferred variant of the coil system according to the invention, the volume in the working space is selected so as to encompass an estimated position of the magnetic body in the working space and a predetermined surrounding area around the estimated position. For example, a user can specify, through a user interface of the coil system, where in the working chamber the magnetic body is approximately located. Based on this input, a predetermined surrounding area is then established around the estimated position in which, in turn, the aforementioned number of positions are established. According to the invention these positions are established to ensure that, a force is generated in a suitable direction and where applicable a magnetic field is generated in a suitable direction for the desired movement or alignment of the magnetic body that on the magnetic body which is located at or in the vicinity of one of the positions. In particular when the coil system is being used for capsule endoscopy the user recognizes in which area of the patient's body the capsule is located on the basis of the images captured by the camera in the capsule, with the result that the user is able to estimate, using the interface, the position, or a corresponding surrounding area, at which the capsule is approximately situated.

The volume in which the number of positions is situated for which forces or magnetic fields having predefined directions are to be generated preferably has dimensions in the range of a few centimeters. In particular, the maximum spacing between two points at the edge of the volume lies between 0.5 cm and 10 cm. In this situation, the volume is preferably configured as a cuboid or a sphere.

The number of positions for which corresponding forces or magnetic fields having predefined directions are generated can be chosen freely. The higher the number is, the better will a homogeneous direction of force or a homogeneous magnetic field direction in the volume considered be ensured. Preferably, at least eight positions are taken into account.

In a preferred embodiment, the currents set in the multiple coils in order to generate the force on the magnetic body in the predefined direction of force constitute the solution to an optimization problem with the boundary condition that the magnitude of the force component of the force on the magnetic body in the predefined direction of force at the number of positions exceeds a predetermined value or lies in a range between two positive values. In this manner it is ensured that a sufficiently large force component is present in the predefined direction of force in order to bring about a movement of the magnetic body in this direction. In this situation, the optimization problem is preferably configured so that the force components of the force on the magnetic body are minimized in two directions that are perpendicular to one another and to the predefined direction of force at the number of positions.

In a further variant of the invention, in which furthermore the alignment of the magnetic body in a predefined orientation direction is achieved, a further constraint on the optimization problem is that the magnitude of the magnetic field component of the magnetic field in a matching direction, corresponding to the predefined orientation direction at the number of positions, exceeds a predetermined value or lies in a range between two positive values. In this situation, the optimization problem is preferably, among other things, the minimization of the magnetic field components of the magnetic field in two directions corresponding to one another and to the matching direction and in particular the orientation direction at the number of positions.

In a preferred embodiment, the minimization of the force components and/or magnetic field components described above is the minimization of a positive value, with the respective force components and/or magnetic field components at the number of positions not being permitted to exceed the positive value in terms of magnitude.

In a further preferred embodiment of the invention, a further constraint taken into account with regard to the solution of the optimization problem is that the currents in the multiple coils lie below respective maximum values in terms of magnitude.

Where applicable, in the solution of the optimization problem the currents in the multiple coils can be weighted differently. Instead of the 2-norm of the vector of the coil currents, in this situation for example the 2-norm of a weighted vector of the coil currents is taken into account, with each individual coil current being weighted with the square root of the ohmic resistance of the coil. The total ohmic power loss in the multiple coils is minimized by this procedure.

The optimization problem described above can be a linear program that can be solved using known convex optimization methods.

In a further embodiment of the coil system according to the invention, the current control unit takes into account a movement of the magnetic body with two translatory degrees of freedom or less.

In a preferred embodiment, the coil system according to the invention is used in a medical device, and in this case the magnetic body is designed as a probe and the device is configured such that a patient to be examined can be positioned into the working space of the coil system and the probe for examining the organs of the patient can be navigated in contact-free fashion by means of the current control unit of the coil system. The medical device is preferably a device for capsule endoscopy, and in this case the probe is a capsule that has an imaging system for capturing images of the internal organs of the patient and a transmit module for sending the captured images to an extracorporeal receiver.

In addition to the coil system described above, the invention furthermore relates to a method for the contact-free magnetic navigation of a magnetic body in a working space with the use of the inventive coil system described above. In this method, in order to generate a force on the magnetic body in a predefined direction of force, the currents in the multiple coils are set so that the direction of the force generated by the currents on the magnetic body at any position of a number of positions in a volume in the working chamber essentially corresponds to the predefined direction of force. The method can implement all the preferred variants described above with reference to the setting of the currents and/or the solution of an optimization problem.

DESCRIPTION OF THE PREFERRED EMBODIMENTS

Figure 3:
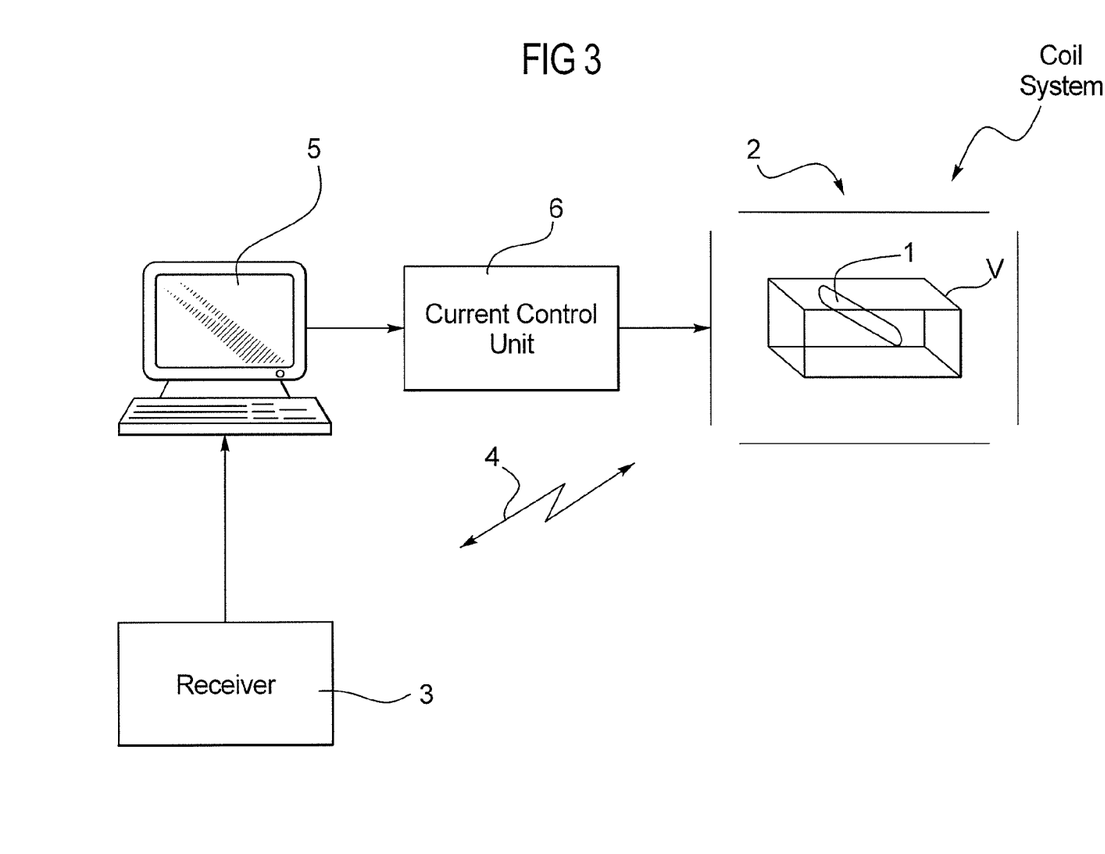
FIG. 3 schematically illustrates a medical device constructed and operating in accordance with the present invention.

The invention will be described in the following with reference to a medical unit for the endoscopic examination of organs of a patient, schematically shown in FIG. 3. The medical unit has a coil system 2 and a magnetic capsule 1 with a magnetic dipole moment that is generated for example by means of a permanent magnet in the capsule. The coil system 2 generates a magnetic field that exerts magnetic forces and a turning moment on the capsule through interaction with the magnetic moment of the capsule. The magnetic dipole moment of the capsule is depicted by the vector m.

By means of a current control unit 6 the magnetic field of the coil system 2 and thus the magnetic forces and the turning moment acting on the capsule 1 are suitably controlled in order to enable changes in the position and orientation of the capsule in a predetermined working volume. In this situation, the capsule contains a camera for capturing images of internal organs of a patient and a transmit module for conveying the captured images to an external receiver 3, as indicated by arrow 4. The capsule 1 is swallowed by the patient to be examined, who is subsequently positioned in the working space of the coil system 2, in other words in a space portion in which the magnetic fields of the coil system 2 exert corresponding forces and turning moments on the capsule.

The medical unit is used for examining the gastro-intestinal tract of a patient. Gastroenterological examinations can be made, for example. The patient drinks a sufficient quantity of water before, and if necessary, also during the examination so that the capsule the patient has swallowed is moved in the water or on the surface of the water in the stomach during the examination. By setting currents appropriately in the coils of the coil system it is then possible to move the capsule on the water surface to the areas in the stomach to be examined and to orient the capsule, and close-up images with the capsule situated entirely in the water beneath the water surface can also be captured. As mentioned above, the captured images are sent by a transmit module to a receiver 6 outside the patient, whereby this receiver is integrated for example in a belt which the patient wears during the examination.

The coil system described in the published application WO 2006/092421 A1 can be employed, for example, as the coil system for use in the embodiment described in the following. This coil system has 14 individually controllable coils for generating corresponding magnetic fields. Other coil systems may also be used, but as a minimum eight single coils are preferably used, in order to control all magnetic degrees of freedom independently of one another for moving the capsule in the working chamber. Although the coil system according to the invention may, where applicable, have the same structure as known coil systems, the coil system according to the invention differs from known coil systems in the means used to control the currents of the individual coils.

In the following description it is assumed that the magnetic forces and turning moments torques that are exerted on the capsule 1 enable the capsule to move with five degrees of freedom or with six degrees of freedom in at least one part of the working volume of the coil system. In this situation, the movement with five degrees of freedom encompasses two degrees of translatory freedom and three degrees of rotatory freedom and corresponds to the application wherein the capsule is moved along the water surface in the stomach of the patient during a gastroenterological examination. In this situation, the degrees of freedom in the working space are characterized by the fact that no significant unknown mechanical forces or turning moments are acting against the magnetic forces and turning moments generated by the coil system in the respective directions of movement of the individual degrees of freedom. Such mechanical counteracting forces occur, for example, as frictional forces, or counteracting forces when a capsule moves along the stomach wall or bumps into the stomach wall.

In the embodiment of the invention described in the following, the currents of the coil system are controlled such that the capsule is aligned in a predetermined direction and moves in a predetermined direction. In this situation, the direction can be set by the operator of the coil system in a suitable manner by a user interface 5. It is not a requirement that the position of the capsule in the body of the patient be determined exactly in order to calculate the suitable currents in the coils of the coil system. It is thus possible—in contrast to known current control facilities—to dispense with a measuring (detection) unit for determining the position of the capsule in the patient's body. Rather, it is sufficient that the position of the capsule can be suitably estimated. The estimation of the position can be achieved, for example, based on the images received from the camera in the capsule, from which images, shown at the user interface 6, it can be seen in which area of the patient's body the capsule is approximately situated.

Figure 1:
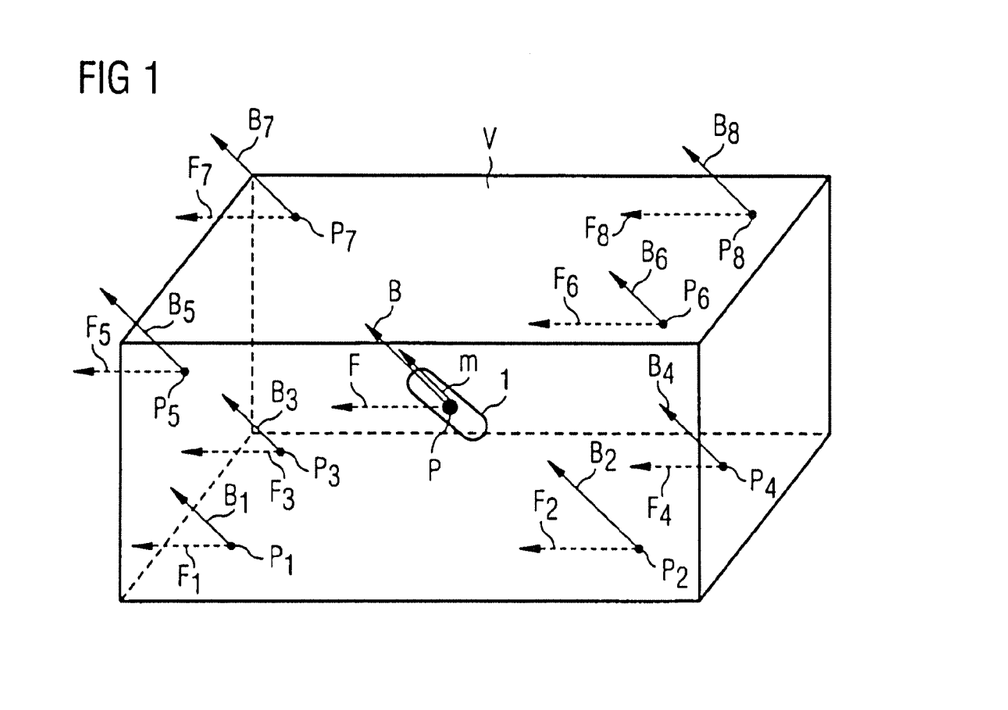
FIG. 1 is a schematic illustration of the forces or magnetic fields generated using an embodiment of the coil system according to the invention.

In order to achieve the alignment and movement of the capsule in predetermined directions, a volume V around this position is predefined for an estimated position of the capsule, and the current control unit 6 serves to ensure that the direction of the magnetic field and the direction of the force exerted on the capsule is constant (uniform) for a number of positions of the capsule in the volume. This scenario is illustrated again with reference to FIG. 1. The estimated position of the capsule is indicated by P. In addition, a magnetic field acting at the position P is indicated by the vector B and a force acting on the capsule at the position P is indicated by the vector F. In this situation, the magnetic field B is a base field, with which a desired alignment of the capsule is achieved. Moreover, this field has superimposed on it a magnetic gradient field that causes the force F to be generated at the position P. Around the position P is defined a volume V that is part of the working volume of the coil system 2. In the example shown in FIG. 1 the volume in question is cuboid. In this situation, the dimensions of the volume are in the range from about 0.5 cm to 10 cm. This means that the spacing of the individual opposite walls of the cuboid shown in FIG. 1 is in this value range as well.

A number of positions $P_1, P_2, \ldots, P_8$ is predefined inside the volume V and it is now the purpose of the current control unit for the coils to ensure for all these positions that the directions of the respective forces $F_1, F_2, \ldots, F_8$, that are acting on the capsule when the capsule is located at the respective positions $P_1, P_2, \ldots, P_8$, essentially match and that furthermore also the directions of the magnetic fields $B_1, B_2, \ldots, B_8$ are essentially the same at the respective positions $P_1, P_2, \ldots, P_8$. Given a sufficiently large number of positions in the volume V this ensures that a capsule, for which only an estimated position P is known, moves and is aligned in a predefined direction as long as the actual position of the capsule lies within the volume V. In the embodiment shown in FIG. 1 the volume V encompasses eight positions for which the condition of a constant magnetic field direction and direction of force should be guaranteed. Depending on the application, however, it is also possible to consider more or fewer positions.

In the following, the force F acting on the capsule 1 at the position P and the magnetic field B generated at this position will first be described generally, based on the coil currents of a coil system. In this situation, vector notation is used for the magnetic field B, the force F and the magnetic moment m because these variables are three-dimensional vectors.

The 3×1 magnetic field vector of the magnetic field $\vec{B}(P)$ and the 3×1 force vector $\vec{F}(P,\vec{m})$ of the force acting on the capsule depend on the currents I of the coils of a coil system, represented as $n_{coils} \times 1$ vector ($n_{coils}$=number of coils of the coil system), as follows:

$$\begin{bmatrix} \vec{B} \\ \vec{F} \end{bmatrix} = A(P, \vec{m})I$$

where $A(P,\vec{m})$ is a $6 \times n_{coils}$ matrix which is a product of two matrices $U(\vec{m})$ and $V(P)$, in other words the following applies:

$$A(P,\vec{m}) = U(\vec{m})V(P)$$

The matrix v(P) is an $8 \times n_{coils}$ matrix which depends not only on the specific spatial position P but also on the geometry of the coil system. In this situation, the matrix is predefined, or can be easily ascertained from the specific geometry of the coil system according to the Biot-Savart law for any desired spatial positions. The further matrix $U(\vec{m})$ is a 6×8 matrix, as follows:

$$U(\vec{m}) = \begin{bmatrix} 1 & 0 & 0 & 0 & 0 & 0 & 0 & 0 \\ 0 & 1 & 0 & 0 & 0 & 0 & 0 & 0 \\ 0 & 0 & 1 & 0 & 0 & 0 & 0 & 0 \\ 0 & 0 & 0 & m_x & m_y & m_z & 0 & 0 \\ 0 & 0 & 0 & 0 & m_x & 0 & m_z & m_y \\ 0 & 0 & 0 & -m_z & 0 & m_x & m_y & -m_z \end{bmatrix}$$

where $m_x$, $m_y$, $m_z$ represent the x, y and z components of the magnetic dipole vector in of the capsule 1.

The magnetic dipole moment $\vec{m}$, in other words the orientation of the capsule, must be known in order to calculate the matrix $U(\vec{m})$. In the following a scenario is considered in which the capsule can move in the space with all three degrees of rotatory freedom. As a result, the magnetic dipole moment of the capsule essentially (in other words with a negligible error) aligns itself in the direction of the magnetic field $\vec{B}$ of the coil system acting on the capsule. To ensure this, a constraint is predefined that the magnitude of the magnetic field be greater than a minimum value, in other words the following applies:

$$\|\vec{B}\| \geq B_{min}$$

where $B_{min}$ is a suitably chosen scalar value which is chosen to be of such a size that the greatest possible disturbing turning moment which may act on the capsule, divided by the product of $B_{min}$ and the magnitude $\vec{m}$, is less than the sine of the maximum permissible spatial angle between $\vec{B}$ and $\vec{m}$.

The magnetic dipole moment $\vec{m}$ of the capsule is known. The relationship between the magnetic field or the force exerted and the current vector at the specific spatial position P can thus be written as follows:

$$\begin{bmatrix} \vec{B} \\ \vec{F} \end{bmatrix} = A(P)I$$

The purpose of the current control unit is now to establish a magnetic base field and a suitable gradient field in the volume V shown in FIG. 1 by setting the corresponding currents in the single coils in such a manner that forces acting in the same direction and also magnetic fields acting in the same direction are generated at a plurality of positions $P_1, \ldots, P_n$, where n is a natural number and n=8 in the example shown in FIG. 1. In this situation, the problem of the corresponding calculation and setting of the currents in the coils of the coil system can be formulated as a convex optimization problem. Convex optimization problems can be solved reliably and efficiently using standard methods. On the basis of the above matrix A(P), the first three rows of the matrix are responsible for setting the magnetic field depending on the current vector I and the last three rows of the matrix describe the generation of the force depending on the current vector I. The positional dependence of the generated magnetic field, or of the generated force, is contained in the matrix A(P) in this situation. The following relationship thus applies:

$$\vec{B}(P,I) = A_{1:3}(P)I$$

$$\vec{F}(P,I) = A_{4:6}(P)I$$

where the notation $A_{i:j}$ denotes a matrix which is composed of rows i to j of the matrix A(P).

In order to now generate a desired magnetic field in a predetermined first direction and a desired force in a predetermined second direction at a point P, a desired magnetic field $\vec{B}_{desired}$ and a desired force $\vec{F}_{desired}$ are predefined. In this situation, the direction of this magnetic field or this force corresponds to the direction of magnetic field and force desired in the corresponding application. In this situation, the magnitude of magnetic field and force is chosen to be of a size such that the alignment of the capsule and the movement of the capsule are ensured, so it is possible to control, by the size of the magnitudes of the magnetic field and the force, how quickly the alignment and movement of the capsule should take place.

In order to align the magnetic field or the force in the desired direction, in the embodiment described here a coordinate transformation of the Cartesian coordinate system predefined for the working chamber of the coil system is performed in such a manner that the desired force vector or magnetic field vector points in the x direction in the transformed coordinate system. This is illustrated again with reference to FIG. 2. In this situation, the original coordinate system is depicted with the x, y and z axes of the working chamber. In the case of medical units for performing capsule endoscopy the z axis preferably denotes the longitudinal axis of a patient located on a patient table, whereas the y direction represents the vertical direction (in other words the direction in which the force of gravity acts) and the x direction extends perpendicular to the longitudinal direction of the patient parallel to the patient table.

Figure 2:
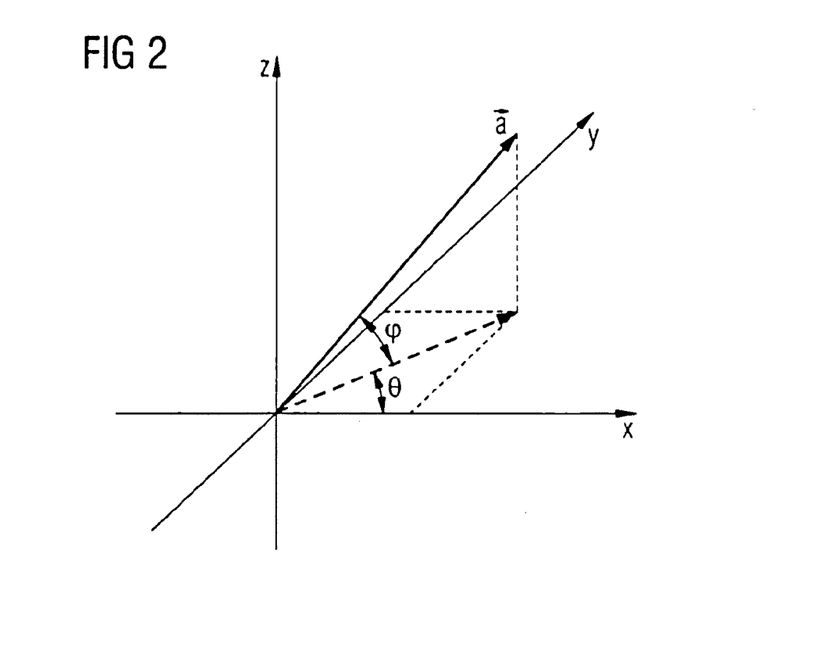
FIG. 2 is a schematic illustration of a Cartesian coordinate system and corresponding rotation angles, as are used for calculating rotation matrices in an embodiment of the coil system according to the invention.

In FIG. 2, either the desired $\vec{B}_{desired}$ magnetic field vector or the desired $\vec{F}_{desired}$ force field vector is designated as the vector $\vec{a}$. The alignment of the vector $\vec{a}$ within the Cartesian coordinate system is described by the angle θ in the x-y plane and the angle ϕ which depicts the alignment of the vector $\vec{a}$ in a plane running perpendicular to the x-y plane. By means of the rotation matrices $R_{z,\theta}(\vec{a})$ and $R_{y,\phi}(\vec{a})$ defined in the following, a rotation of the coordinate system shown in FIG. 2 is described, initially around the z axis by the angle θ and then around the y axis by the angle ϕ:

$$R_{z,\theta}(\vec{a}) = \begin{bmatrix} \cos(\theta) & -\sin(\theta) & 0 \\ \sin(\theta) & \cos(\theta) & 0 \\ 0 & 0 & 0 \end{bmatrix}$$

$$R_{y,\varphi}(\vec{a}) = \begin{bmatrix} \cos(\varphi) & 0 & -\sin(\varphi) \\ 0 & 1 & 0 \\ -\sin(\varphi) & 0 & \cos(\varphi) \end{bmatrix}$$

The vector $\vec{a}^*$ in the correspondingly transformed coordinate system thus is expressed as follows:

$$\vec{a}^* = R_{y,\phi}(a) R_{z,\theta}(\vec{a}) \vec{a}$$

This vector has the same magnitude as the vector $\vec{a}$, but has only one further non-zero x component $\vec{a}_x^*$.

For any point P in the working chamber of the coil the following value $\vec{B}^*(P,I)$ thus results in the correspondingly transformed coordinate system for a corresponding desired magnetic field whose alignment is described by the angles ϕ and θ:

$$\vec{B}^*(P,I) = R_{y,\theta}(\vec{B}_{desired}) R_{z,\theta}(\vec{B}_{desired}) A_{1:3}(P) I$$

Similarly, for a force at a point P in the working chamber, which force is aligned in the corresponding angle directions ϕ and θ, the following value $\vec{F}^*(P,I)$ results in the transformed coordinate system:

$$\vec{F}^*(P,I) = R_{y,\phi}(\vec{F}_{desired}) R_{z,\theta}(\vec{F}_{desired}) A_{4:6}(P) I$$

In this situation, the values of θ and ϕ for the force may differ from the values of θ and ϕ for the magnetic field. On the basis of the above equations it is now possible to define a suitable optimization problem in such a way that the correspondingly transformed magnetic field $\vec{B}^*$, which originates from the desired magnetic field $\vec{B}_{desired}$ and the correspondingly transformed force vector $\vec{F}^*$, which originates from the desired force vector $\vec{F}_{desired}$ exhibit the corresponding magnitude of the magnetic field vector $\vec{B}_{desired}$ or of the force vector $\vec{F}_{desired}$ as a minimum magnitude in the x direction, whereas the y and z components of the magnetic field vector $\vec{B}^*$ or of the force vector $\vec{F}^*$ should be as small as possible.

In the embodiment described here, an additional auxiliary condition furthermore takes into account the fact that the absolute values of the currents in the single coils should be less than respective maximum values. In this situation it is assumed in the following that the maximum current in all coils should be equally great, whereby this current is designated by $I_{max}$. It is however also possible to predefine separate, differing maximum values for the currents in the single coils.

The optimization problem considered in the embodiment described here can generally be described as a minimization problem for points $P_1, P_2, \ldots, P_n$ in a volume V in such a manner that an ϵ is sought for predefined variables $\vec{B}_{desired}$, $\vec{F}_{desired}$ and $I_{max}$, such that the following applies:

$$\min_{I,\varepsilon} \varepsilon$$

$$\varepsilon > 0$$

$$B_x(P_1, I) > \|\vec{B}_{desired}\|$$

$$\varepsilon < B_y(P_1, I) < \varepsilon$$

$$\varepsilon < B_z(P_1, I) < \varepsilon$$

$$F_x(P_1, I) > \|\vec{F}_{desired}\|$$

$$\varepsilon < F_y(P_1, I) < \varepsilon$$

$$\varepsilon < F_z(P_1, I) < \varepsilon$$

$$\vdots$$

$$B_x(P_n, I) > \|\vec{B}_{desired}\|$$

$$\varepsilon < B_y(P_n, I) < \varepsilon$$

$$\varepsilon < B_z(P_n, I) < \varepsilon$$

$$F_x(P_n, I) > \|\vec{F}_{desired}\|$$

$$\varepsilon < F_y(P_n, I) < \varepsilon$$

$$\varepsilon < F_z(P_n, I) < \varepsilon$$

$$I_{max} < I < I_{max}, \text{ by component}$$

An optimization problem is thus given in such a manner that a minimum positive ϵ is sought, such that the transformed B field is as small as possible in the y direction and the z direction and also that the transformed force is as small as possible in the y direction and the z direction, namely under the condition that the transformed B field in the x direction and the transformed force in the x direction exceed a predetermined value. At the same time, the condition that the current in each coil does not exceed a maximum value must be satisfied. The deviation of the ascertained magnetic field or of the ascertained force vector from the desired direction is quantified through the above ϵ, and this deviation is kept as small as possible through the minimization condition. The above conditions on the B field or on the force are depicted in accordance with the preceding inequations only for the points $P_1$ and $P_n$. Corresponding equations also exist for the further points $P_2, \ldots, P_{n-1}$, which is indicated by means of a vertical ellipsis comprising three points in the above system of inequations.

The above system of inequations can also be suitably modified in a further variant of the invention, namely in such a manner that not a minimum value is predefined as the condition for the magnetic field or the force in the x direction but a range of values, within which the corresponding x component must lie. The optimization problem described above and the constraints are linear, which means that this problem is a linear program which can be solved by using methods known from the prior art.

As emerges from the above statements, in a variant of the coil system according to the invention the current control unit is configured in such a manner that, based on the solution of an optimization problem, a magnetic field and a force acting on the capsule are generated in a volume around an estimated capsule position in a direction which matches a desired direction as well as possible. In this manner, it is also possible without the exact determination of a capsule position to ensure by means of a measuring device that a capsule is moved in a predetermined direction and is aligned in a predetermined direction through corresponding energization of the coil system. When operating the coil system by way of a corresponding user interface it is sufficient in this situation for a volume in which the capsule is located to be specified only roughly. Subsequently, based on an alignment and direction of movement of the capsule specified by the user by way of the user interface, the corresponding currents are set in such a manner that the capsule rotates into the desired alignment and moves in the desired direction.

In the embodiment described above of the current control unit according to the invention the currents are calculated in real time after corresponding setting of the desired alignment of the capsule and the desired direction of movement of the capsule. It is also possible, however, for a multiplicity of alignments and directions of movement of the capsule and a multiplicity of estimated capsule positions in the working chamber of the coil, for the corresponding currents to be set to have been ascertained in advance and stored in a memory in the current control unit. In this case, after the desired alignment and direction of movement of the capsule have been set the currents of the individual coils to be used for this purpose are read out from the memory and set by the current control unit.

Although modifications and changes may be suggested by those skilled in the art, it is the intention of the inventors to embody within the patent warranted hereon all changes and modifications as reasonably and properly come within the scope of their contribution to the art.

We claim as out invention:

1. A coil system for contact-free magnetic navigation of a magnetic body with a magnetic dipole moment in a working space, comprising:
   a plurality of coils respectively located at different positions surrounding the working space;
   a current control unit that controls respective currents in the plurality of coils;
   a user interface in communication with said current control unit and with said magnetic body, said user interface being configured to allow a user to identify, from information provided to said user interface by said magnetic body, a position of said magnetic body within said working space, and to estimate and define an edge of a volume, having a size between 0.5 cm and 10 cm, in said working space, said volume surrounding an estimated position of the magnetic body in said working space determined from information communicated to said user interface from said magnetic body, and said user interface being configured to communicate information defining said volume to said current control unit; and
   said current control unit being configured, in response to said information from said user interface, to generate a force on the magnetic body in a predefined direction by setting the currents in the plurality of coils to produce a magnetic field in said volume that causes a direction of a force on the magnetic body produced by said magnetic field at each position among a plurality of positions of the magnetic body in the volume to be uniform in said volume and to substantially correspond to the predefined direction of force.

2. The coil system as claimed in claim 1, wherein the current control unit is configured, in response to said information from said user interface, to set said currents to align the magnetic body in a predefined orientation direction by setting the currents in the plurality of coils to cause respective directions of the magnetic field generated by the currents at each position of the magnetic body among the plurality of positions in the volume to substantially match and cause alignment of the magnetic body in the predefined orientation direction.

3. The coil system as claimed in claim 2, wherein the current control unit is configured, in response to said information from said user interface, to set said currents to cause the direction of the magnetic field generated by the currents at each position of the magnetic body among the plurality of positions in the volume to correspond substantially to the predefined orientation direction.

4. The coil system as claimed claim 1, wherein said current control unit is configured, in response to said information from said user interface, to set the currents to align the magnetic body in the volume with said predefined orientation for at least eight positions of said magnetic body in said volume.

5. The coil system as claimed in claim 1, wherein said current control unit is configured, in response to said information from said user interface, to set the currents in order to generate the force on the magnetic body in the predefined direction of force as a solution to an optimization problem with a constraint that a magnitude of a force component of the force on the magnetic body in the predefined direction of force at the plurality of positions exceeds a predetermined value or is in a range between two positive values.

6. The coil system as claimed in claim 5, wherein said current control unit is configured to implement, as said optimization problem, minimization of force components of the force on the magnetic body in two directions that are perpendicular to one another and to the predefined direction of force at the plurality of positions.

7. The coil system as claimed in claim 5, wherein said current control unit is configured to set said currents in order to align the magnetic body in the predefined orientation direction with a further constraint in the optimization problem that the magnitude of a magnetic field component of the magnetic field in a direction corresponding to the predefined orientation direction at the plurality of positions exceeds a predetermined value or is in a range between two positive values.

8. The coil system as claimed in claim 7, wherein said current control unit is configured to implement, as said optimization problem, minimization of magnetic field components of the magnetic field in two directions and to the orientation direction at the plurality of positions.

9. The coil system as claimed in claim 8, wherein said current control unit is configured to implement, as said minimization of the force components and/or magnetic field components, by minimization of a positive value, with the respective force components and/or magnetic field components at the plurality of positions not being permitted to exceed the positive value in terms of magnitude.

10. The coil system as claimed in claim 5, wherein said current control unit is configured to solve said optimization problem with a further constraint that the currents in the plurality of coils are below respective maximum values in terms of magnitude.

11. The coil system as claimed in claim 5, wherein said current control unit is configured to solve said optimization problem with the currents in the plurality of coils weighted differently.

12. The coil system as claimed in claim 5, wherein said current control unit is configured to implement, as said optimization problem, a linear program.

13. The coil system as claimed in claim 1, wherein said current control unit, in response to said information from said user interface, is configured to set said current while allowing for movement of the magnetic body with two translatory degrees of freedom or less.

14. A medical device comprising:
a probe comprising a magnetic body;
a coil system comprising a plurality of coils respectively located at different positions surrounding a working space in which said probe comprising said magnetic body is navigated by contact-free magnetic navigation;
a current control unit that controls respective currents in the plurality of coils;
a user interface in communication with said current control unit and with said magnetic body, said user interface being configured to allow a user to identify, from information provided to said user interface by said magnetic body, a position of said magnetic body within said working space, and to estimate and define an edge of a volume, having a size between 0.5 cm and 10 cm, in said working space, said volume surrounding an estimated position of the magnetic body in said working space determined from information communicated to said user interface from said magnetic body, and said user interface being configured to communicate information defining said volume to said current control unit; and
said current control unit being configured, in response to said information from said user interface, to generate a force on the magnetic body in a predefined direction by setting the currents in the plurality of coils to produce a magnetic field in said volume that causes a direction of a force on the magnetic body produced by said magnetic field at each position among a plurality of positions of the magnetic body in the volume in to be uniform in said volume and to substantially correspond to the predefined direction of force.

15. A medical device as claimed in claim 14 wherein said probe comprises a capsule containing an imaging unit that captures images of internal organs of the patient, and a transmit module that sends the captured images to an extracorporeal receiver in communication with said user interface, and wherein said user interface is configured to display said images to allow said user to estimate said position of said magnetic body.

16. A method for operating a coils system for contact-free magnetic navigation of a magnetic body with a magnetic dipole moment in a working space, comprising:
providing a plurality of coils respectively located at different positions surrounding the working space;
with a current control unit, controlling respective currents in the plurality of coils;
via a user interface in communication with said current control unit and with said magnetic body, allowing a user to identify, from information provided to said user interface by said magnetic body, a position of said magnetic body within said working space, and to estimate and define an edge of a volume, having a size between 0.5 cm and 10 cm, in said working space, said volume surrounding an estimated position of the magnetic body in said working space determined from information communicated to said user interface from said magnetic body, and communicating information defining said volume from said user interface to said current control unit;
in said current control unit, in response to said information from said user interface, generating a force on the magnetic body in a predefined direction by setting the currents in the plurality of coils to produce a magnetic field in said volume that causes a direction of a force on the magnetic body produced by said magnetic field at each position among a plurality of positions of the magnetic body in the volume to be uniform in said volume and to substantially correspond to the predefined direction of force.

17. A method as claimed in claim 16 comprising, with an in vivo imaging unit, obtaining images of internal organs of the patient, sending the captured images to an extracorporeal receiver in communication with said user interface, and at said user interface, displaying said images to allow said user to estimate said position of said magnetic body.

* * * * *